(12) United States Patent
Belongia

(10) Patent No.: US 7,578,205 B2
(45) Date of Patent: Aug. 25, 2009

(54) STERILE SAMPLING DEVICE

(75) Inventor: Brett M. Belongia, North Andover, MA (US)

(73) Assignee: Millipore Corporation, Billerica, MA (US)

( * ) Notice: Subject to any disclaimer, the term of this patent is extended or adjusted under 35 U.S.C. 154(b) by 481 days.

(21) Appl. No.: 11/441,910

(22) Filed: May 26, 2006

(65) Prior Publication Data
US 2006/0272432 A1   Dec. 7, 2006

Related U.S. Application Data

(60) Provisional application No. 60/686,377, filed on Jun. 1, 2005.

(51) Int. Cl.
*G01N 1/00* (2006.01)
(52) U.S. Cl. .................. 73/863.11; 73/863.86
(58) Field of Classification Search .............. 73/863.31, 73/863.86
See application file for complete search history.

(56) References Cited

U.S. PATENT DOCUMENTS

| | | | |
|---|---|---|---|
| 1,831,457 A | 11/1931 | Larsen | |
| 2,736,201 A | 2/1956 | Ohlsen et al. | |
| 2,844,964 A | 7/1958 | Guibert | |
| 2,865,394 A * | 12/1958 | Presley | 137/334 |
| 3,319,622 A | 5/1967 | Shiner | |
| 3,638,499 A | 2/1972 | Saint-Andre | |
| 3,678,959 A | 7/1972 | Liposky | |
| 3,747,411 A | 7/1973 | McDermott | |
| 3,848,581 A | 11/1974 | Cinqualbre et al. | |
| 3,858,449 A | 1/1975 | Singer | |
| 3,921,456 A * | 11/1975 | Newcomb et al. | 73/863.31 |
| 4,207,922 A | 6/1980 | Andrieux et al. | |
| 4,423,641 A | 1/1984 | Ottung | |
| 4,454,772 A * | 6/1984 | Brunner et al. | 73/863.31 |
| 4,479,393 A | 10/1984 | Shores | |
| 4,569,236 A * | 2/1986 | Kitchen et al. | 73/863.31 |
| 4,580,452 A | 4/1986 | Masson | |
| 4,584,887 A | 4/1986 | Galen | |
| 4,669,312 A | 6/1987 | Maurer | |
| 4,669,321 A | 6/1987 | Meyer | |
| 4,704,910 A * | 11/1987 | Conrad | 73/863.21 |
| 5,161,417 A * | 11/1992 | Strong et al. | 73/863.86 |

(Continued)

FOREIGN PATENT DOCUMENTS

DE   8812723 U1   12/1988

(Continued)

*Primary Examiner*—Robert R Raevis

(57) ABSTRACT

The present invention provides fluid sampling device comprising a sampling head having a series of openings through it from one major surface to the other, a plurality of conduits at the downstream side of the openings and a plurality of sample containers. The openings are selectively opened and closed through the use of switches mounted within each opening and the head of the device members, each switch being movable within said head between closed and open positions. The conduits (e.g., flexible tubing) are equal in number to the openings, with each conduit connected to an individual port fitting arranged on a face of the head downstream of the respective opening. Similarly, the sample containers (e.g., flexible bags) are equal in number to the conduits, with each sample container connected to an individual conduit opposite the connection to the port. A specific configuration for the device, as well as a kit containing pre-sterilized components of the fluid sampling device, are also described.

13 Claims, 3 Drawing Sheets

U.S. PATENT DOCUMENTS

| | | | |
|---|---|---|---|
| 5,296,197 | A | 3/1994 | Newberg et al. |
| 5,375,477 | A * | 12/1994 | Neill et al. ............... 73/863.23 |
| 5,398,557 | A | 3/1995 | Shimizu et al. |
| 5,525,301 | A | 6/1996 | Newberg et al. |
| 5,747,708 | A | 5/1998 | Weiberth |
| 5,786,209 | A | 7/1998 | Newberg |
| 5,829,425 | A | 11/1998 | Woods et al. |
| 5,911,252 | A | 6/1999 | Cassel |
| 5,948,998 | A | 9/1999 | Witte et al. |
| 6,032,543 | A | 3/2000 | Arthun et al. |
| 6,133,022 | A | 10/2000 | Newberg |
| 6,345,640 | B1 | 2/2002 | Newberg |
| 6,386,137 | B1 | 5/2002 | Riche |
| 6,477,906 | B1 | 11/2002 | Peterson |
| 6,516,677 | B1 | 2/2003 | Suter |
| 6,779,575 | B1 | 8/2004 | Arthun |
| 6,860,162 | B1 | 3/2005 | Jaeger |
| 2003/0188588 | A1 | 10/2003 | Jaeger |
| 2005/0132821 | A1 | 6/2005 | Furey et al. |

FOREIGN PATENT DOCUMENTS

| | | |
|---|---|---|
| EP | 0107579 | 5/1984 |
| EP | 0154002 | 9/1985 |
| EP | 0508749 | 10/1992 |
| WO | WO 03090842 | 11/2003 |

* cited by examiner

STERILE SAMPLING DEVICE

CROSS-REFERENCED TO RELATED APPLICATIONS

The present patent application claims the benefit of U.S. Provisional Patent Application No. 60/686,377, filed on Jun. 1, 2005. The entirety of which is incorporated herein.

FIELD

In general, the present invention is directed to a fluid sampling device, and in particular, to a fluid sampling device having a configuration amenable to "single-use disposability", while still enabling sterile sampling, and does not in its operation require the piercing of a septum.

BACKGROUND

When conducting complex and/or delicate fluid processes within a "closed" fluid receptacle, to monitor the progress of the process, it is often desirable to withdraw and analyze samples of the fluid without disturbing the process, such as may occur upon "opening" the receptacle. For example, in the study and/or manufacture of biochemical products (e.g., biopharmaceuticals), biochemical fluid is often contained in an aseptically or sterile "closed" fermenting tank, bioreactor, or like fluid receptacle, wherein the fluid is processed over comparatively long periods of time, under diverse and changing chemical and internal environmental conditions. By withdrawing and analyzing samples of the fluid intermittently in the course of the process, one can learn more about the progress of the process, and if called for, take prophylactic measures to change the outcome thereof.

Similar issues arise also in instances wherein fluid is conducted through a conduit, a pipe, and like fluid receptacle. Sampling of said fluid is often difficult because in many industrial systems, said receptacles are not easily opened or dissembled to allow one to withdraw fluid samples, especially in a sterile manner.

While several fluid sampling techniques are known, certain technical issues can be noted. For example, certain integrated fluid sampling fixtures comprise stainless steel valves and piping which, for biopharmaceutical applications, often require laborious steam sterilization and cleaning prior to use. (See e.g., U.S. Pat. No. 5,948,998). Other fluid sampling devices are difficult to integrate into extant fluid processing systems, for example, by requiring the installation of custom-fitted ports onto a host fluid receptacle. (See e.g., U.S. Pat. No. 6,032,543). Still other devices, although adapted for use in standard industrial ports, are complex and costly instruments comprising valves, inlets, outlets, seals, needles, and other components, all precisely arranged, but capable of only a single aseptic sample per sterilization cycle. (See e.g., U.S. Pat. No. 4,669,312). Finally, the majority of fluid sampling devices—as is the case in many of those already mentioned—require in their operation the piercing of a septum using a hypodermic needle. (See e.g., U.S. Pat. Nos. 6,032,543, 4,423,641 and 2,844,964).

One device exists in which no septum needs to be pierced and which allows for a disposable, sterile multisample port (U.S. Ser. No. 10/746,030 filed Dec. 23, 2003). It consists of a series of movable conduits each having a closed face and an opening sealably positioned behind the closed face. These conduits are arranged in a port insert such that the closed face is at or near the interior surface of the tank or vessel to be sampled. The conduits are moved linearly or rotationally from a closed position to an open position to expose the opening in order to take the sample and are then moved back to the closed position after sampling. The other end of the conduits have a sterile tube connected to it and to a sample bag or vessel. The tube is then sterilely cut and sealed and the sample is then analyzed.

In light of the above, a need exists for a fluid sampling device that is sufficiently inexpensive in its construction to promote single-use disposability, capable of being used in standard industrial ports commonly found in fluid receptacles, and capable of several sterile fluid sample withdrawals per sterilization cycle and/or prior to being exhausted without the use of a piercable septum.

SUMMARY

The present invention provides a fluid sampling device comprising a sampling head, a plurality of sealable ports arranged about the head and a plurality of sample containers connected to the ports on a face that extends outward from the sampling head face that is mounted against the fluid receptacle to be sampled. The sampling head comprises a body having a plurality of openings extending through it from a first major face to a second major face. The first major face is disposed toward the fluid to be sampled and the second major face is disposed away from the fluid and downstream of the first face. Each of the openings on the second major face which is away from the face that attaches to the fluid receptacle to be sampled has an attachment port to which a flexible conduit is attached. Each port has a mechanism for ensuring a secure sterile and leakproof attachment of the flexible conduit to the ports. Each flexible conduit is connected on its downstreamside from the port to a sample holder. Each of the openings adjacent the first major face have a movable gate or switch which selectively covers the opening in a manner allowing movement of said gates between "closed" and "open" positions. The sample containers are preferably flexible bags or syringes; and the conduits; preferably, flexible tubing.

When the sampling head is installed into a suitable port provided on a fluid receptacle, each gate is in its "closed" position and can then be moved into its "open" position, whereupon, fluid contained within the receptacle flows into the opening, then through the flexible conduit, and ultimately into the sample container. After the desired amount of fluid is collected in the sample container, the gate is moved and preferably locked into its "closed" position, the flexible conduit is severed (preferably, in a sterile or at least aseptic manner), and the sample container subjected to further analysis. The process can then be repeated, by using the remaining openings. When all openings have been exhausted, the sampling head is fully spent and can be easily removed and replaced after the fluid processes in the fluid receptacle are concluded.

In light of the above, it is a principal object of the present invention to provide a fluid sampling device.

It is another object of the present invention to provide a fluid sampling device that enables the withdrawal of several samples of fluid from a fluid receptacle.

It is another object of the present invention to provide a fluid sampling device that enables the withdrawal of several samples of fluids from a fluid receptacle, wherein said withdrawal occurs in a sterile manner.

It is another object of the present invention to provide a fluid sampling device that enables the withdrawal of several samples of fluids from a fluid receptacle, the fluid sampling device capable of being configured to allow so-called "single-use disposability".

It is another object of the present invention to provide a fluid sampling device comprising a sampling head having a series of ports, the ports having an attachment mechanism to which a plurality of flexible conduits are connected and a plurality of sample containers (preferably, flexible, bag-like sample containers) connected to the conduits downstream of the attachment mechanisms.

It is another object of the present invention to provide a sampling head insert useful for making a fluid sampling device, said sampling head achieving maximized functionality with a minimized number of comparatively inexpensive components, thus promoting said "single use disposability".

It is another object of the present invention to provide a kit containing in pre-sterilized packaging, the assembled, partially assembled, or unassembled components of a fluid sampling device, wherein all contained components are pre-sterilized.

These and other object of the present invention can be better understood in view of the detailed description herein, read in conjunction with the attached drawings.

DETAILED DESCRIPTION

Figure 1:
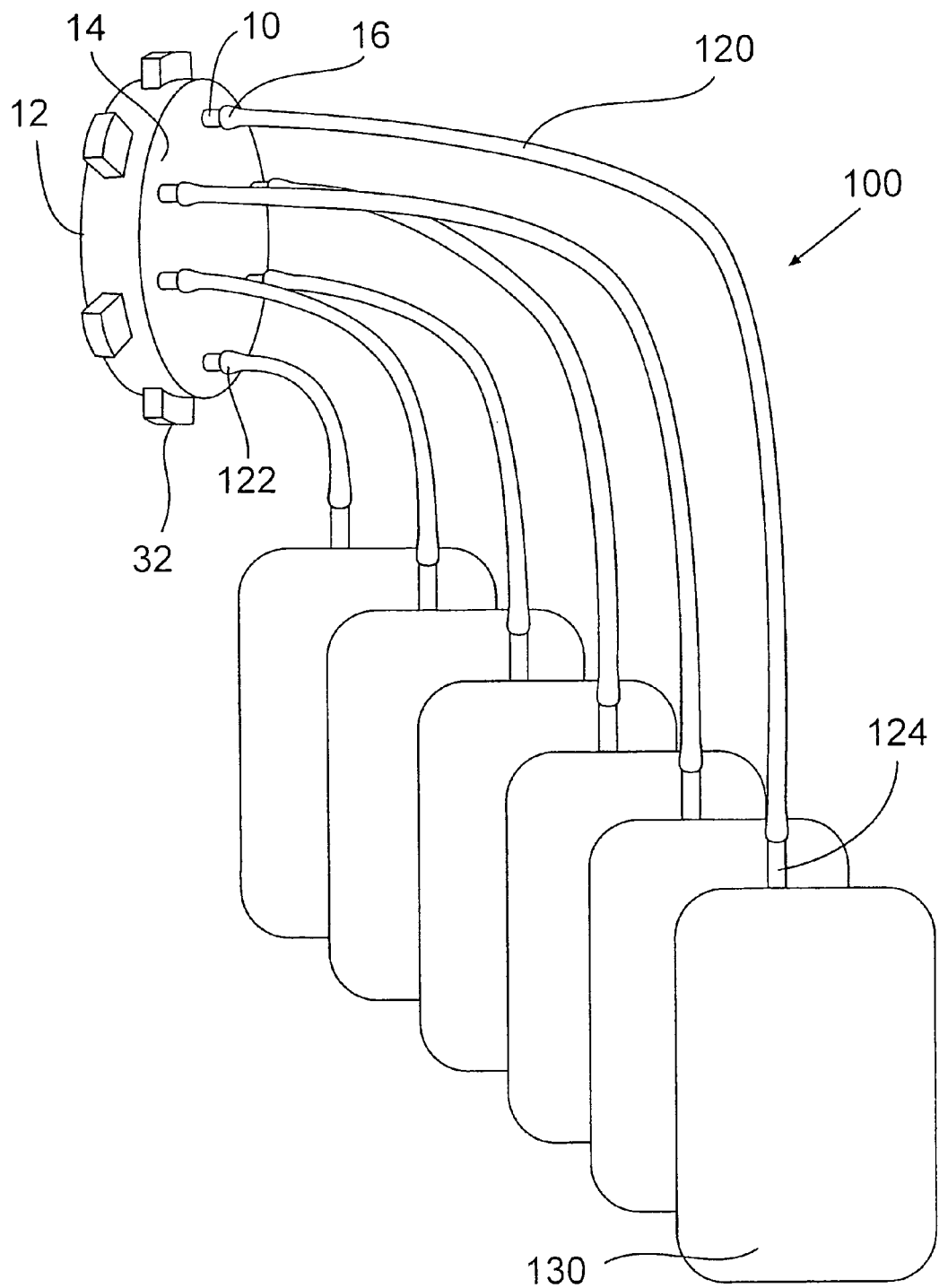
FIG. 1 schematically illustrates a fluid sampling device according to an embodiment of the present invention.
Figure 2:
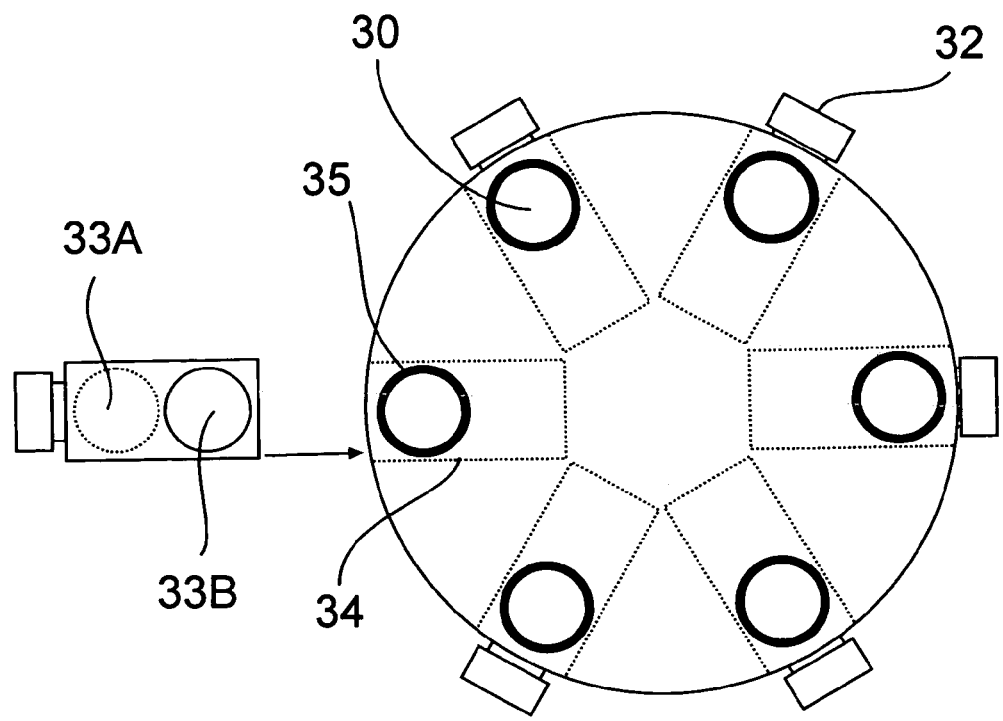
FIG. 2 schematically illustrates an embodiment of the device in top down view.

As illustrated in FIGS. 1 and 2, the fluid sampling device 100 of the present invention comprises, in general, a sampling head 10, a plurality of conduits 120, and a plurality of sample containers 130. When the head 10 is attached to a host fluid receptacle (such as a bioreactor vessel or pipe), samples of fluid can be removed sequentially from the host fluid receptacle, and collected in individual sample containers 130, without substantially disturbing, corrupting, or otherwise affecting any ongoing fluid processes occurring within the host receptacle. Upon completion of said fluid processes, the spent (or partially spent) fluid sampling device 100 is removed, allowing comparatively easy replacement with a fresh unit prior to conducting another of said fluid processes.

The head 10 includes several openings 30 that extend through the thickness of the head 10 from a first major face 12 of the head 10 to a second major face 14 of the head 10. Each opening provides the means through which fluid is withdrawn from the host fluid receptacle into one of said sample container 130. The head 10 also includes a series of ports 16 attached to the openings 30 at or adjacent to the second face 14. The conduits 120 are attached to the ports 16 at a first end 122 of the conduit 120 and to the sample containers 130 at a second end 124 of conduits 120. The openings 30 each have a switch 32 disposed therethrough in a manner allowing movement of said switches 32 between "closed" and "open" positions.

In operation, prior to being charged with fluid, a host fluid receptacle 50 is clean, sterilized, and otherwise prepared for processing. The pre-sterilized fluid sampling device 100 is installed into an existing port or especially made port if desired, provided in the host and its innermost face, the first face 12, to the host receptacle is sterilized in place. The fluid receptacle 50 is then charged with the fluid, and fluid processing commences. During the processing of the fluid, when a sample is desired for analysis, one of the switches 32 is moved from its normally "closed" position into its "open" position, whereupon fluid flows out of the host receptacle, through the selected opening 30, switch opening and port 16 then through the attached fluid conduit 120, and ultimately into the sample container 130. After the desired quantity of fluid is collected, the switch 32 is moved back to its closed position and the conduit 120 can be clamped off at least one, sometimes two points then severed and sealed between the clamp(s) and the sample container 130, so that the captured sample can be removed for analysis. A heat knife, a flame, metal or plastic crimp, such as is taught by U.S. Pat. No. 6,779,575 or other means can be used to sever and seal the conduit. As the fluid process continues, if further samples are desired, another of the remaining unused switches 32 can be activated. This continues until all sample containers 130 are spent, or the fluid process ends. At the end of the fluid process, the fluid sampling device 100 is removed, and disposed of in accordance with appropriate industrial practice. When the host receptacle is again needed for another processing operation, a fresh fluid sampling device 100 is installed.

The fluid sampling device 100 is preferably made as a "single use" item. In this regard, it is "single use" in the sense that at the completion of the desired (or predetermined) number of fluid sampling operations, the device 100 can either be either disposed (e.g., as is sometimes required by law after sampling certain environmentally-regulated substances) or partially recycled (e.g., after dispensing non-regulated substances).

The head 10 has a series of recesses 34 that extend in a plane parallel to the two major surfaces into which the switches 32 reside and operate. The recesses 34 are shaped to form a water-tight seal with the openings 30 and the switches 32 and may use O-rings or gaskets 35 in the recesses 34 (as shown) and/or on the switches 32 to enhance the watertightness. Generally the switches 32 are a flat slide that has a hole 33B equal or less than the diameter of the opening and in align with the opening 30 when in use when in the open position. It also has a closed or solid section 33A that is in position over the opening 30 when in the closed position so as to provide the watertight seal. As the side of the switch facing the second face is connected to the port and the conduit and the sample container, it is always in a sterile condition once the entire structure has been sterilized such as by gas (ETO), steam or autoclave or more preferably radiation such as gamma or beta radiation. The side of the switch facing the first side is sterilized along with the rest of that surface and the receptacle when it is put it place. Typically this is by steaming in place although other means may be used if desired.

The switches 32 may move linearly in and out of the head 10 (as shown in FIG. 2) or they may move rotationally (not shown) to selectively open and close the openings 30. Preferably, they are also designed so that the switch always moves within a sterile area or field so as to prevent the switch movement from bringing in contamination into the sample or the receptacle from which it is drawn. The use of various gasket or O-ring arrangements to ensure sterility are well-known to one of skill in the art and can be used in this invention as well.

In respect of materials and methods, the head 10 will generally be formed monolithically (i.e., as a single, homogenous, unitary, unassembled piece) or if desired or easier for molding purposes as two pieces that are then sealed together.

Preferably in any embodiment the head is made from polymeric material, for example, by well-known injection molding or like processes.

The device may be made of any plastic material capable of withstanding in line steam sterilization. The temperature and pressure of such sterilization is typically about 121° C. and 1 bar above atmospheric pressure. In some instances, it may be desirable to use even harsher conditions such as 142° C. and up to 3 bar above atmospheric pressure. The first face 12, preferably the entire head and the switches should be capable of withstanding these conditions. Preferably, the entire device is made of the same material and is capable of withstanding these conditions. Suitable materials for this device include but are not limited to PEI (polyetherimide), PEEK, PEK, polysulphones, polyarlysulphones, polyalkoxysulphones, polyethersulphones, polyphenyleneoxide, polyphenylenesulphide and blends thereof. Alternatively, one can make the face portion from ceramic or metal inserts alone or that are overmolded with a plastic cover. One can also form a polymeric face with a metal outer layer using plasma coating processes.

To accommodate easy installation of the fluid sampling device into the host receptacles the sampling head 10 is preferably substantially cylindrical in shape and have an external diameter matching that of the port to which it is mounted. One well known and accepted port size is approximately 0.985 inch (2.5 cm.) In the biopharmaceutical field, such configuration will allow the fluid sampling device 100 to be installed, without further custom engineering, into several commercially-available types of bioreactors, that already contain ports (e.g., so-called "Ingold Ports") of such dimensions provided thereon, and which are currently used for probes and other sensors.

Alternatively, a new port can be added to new equipment or retrofitted to older equipment and have a dimension that is larger or smaller than that of the standard Ingold port as is desired. It is contemplated that a larger port may be of particular value if the number of samples is high or the location of sampling being consistent is desirable. One can use a low or almost flush port design such as the NAconnect® port available from Novaseptic AB of Sweden as it minimizes the potential for deadlegging (trapped or stagnant fluid).

Each of the switches 32 are preferably monolithic and rigid and preferably also made of same heat resistant plastic as the head into which they are inserted. They are shaped to fit substantially water-tight within the head 10 and may contain one or more O-rings or gaskets. Alternatively, one or more O-rings or gaskets may be mounted within the slot in the head 10 into which each switch 32 fits.

Figure 3:
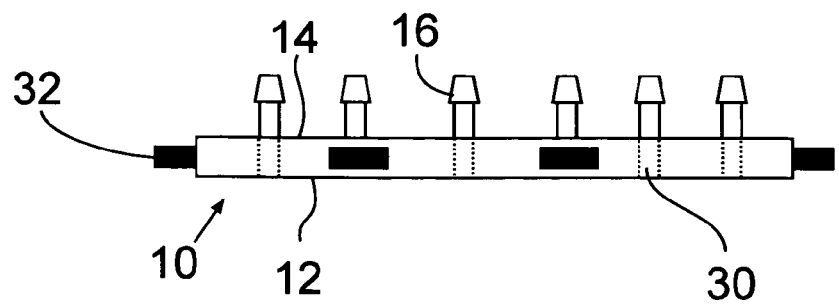
FIG. 3 shows an embodiment of the invention in side view.

A number of openings 30 and switches 32 may be used in the device 100 and are only limited by the ability to mount each of them in the head 10 effectively. Generally, at least one, preferably at least 4, more preferably from 4-12 may be used in each head 10. In a desirable embodiment, six openings 30, each having a diameter of 0.25 inch, are provided on the head 10. As shown in FIGS. 2 and 3, each opening 30 is preferably configured as a cylindrical fluid passage way running substantially the entire length from the first face 12 to second face 14. The opening(s) being "uncovered" or otherwise made accessible to fluid only when the switch 32 in the respective opening 30 is moved into its "open" position exposing the hole 33B. The internal diameter of such hollow passage is in the range of approximately 0.125 inch to approximately 1.0 inch.

Figure 4:
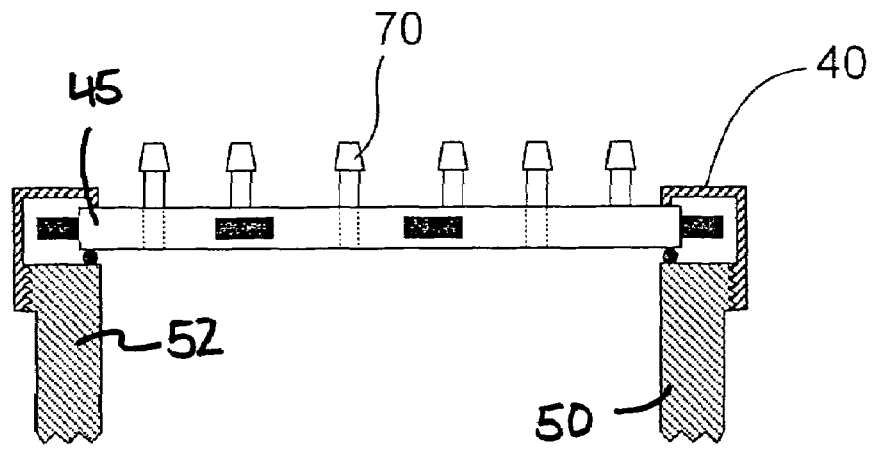
FIGS. 4, 4A and 4B shows additional embodiments of the invention in side view with a means for attaching the device to a port of a fluid receptacle.
Figure 4A:
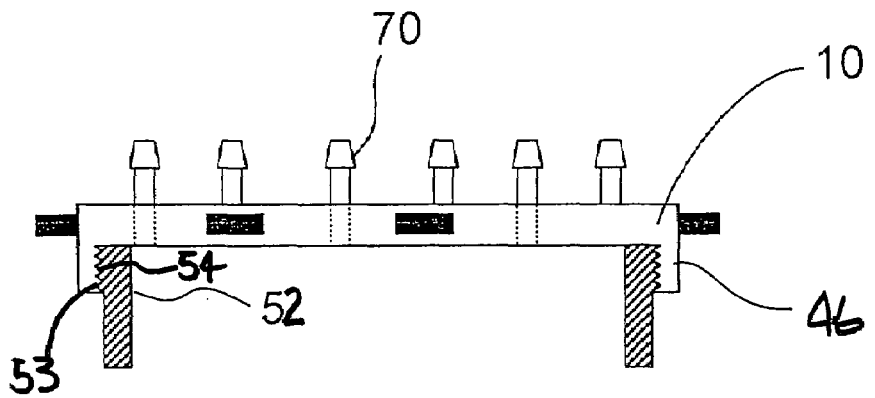
Figure 4B:
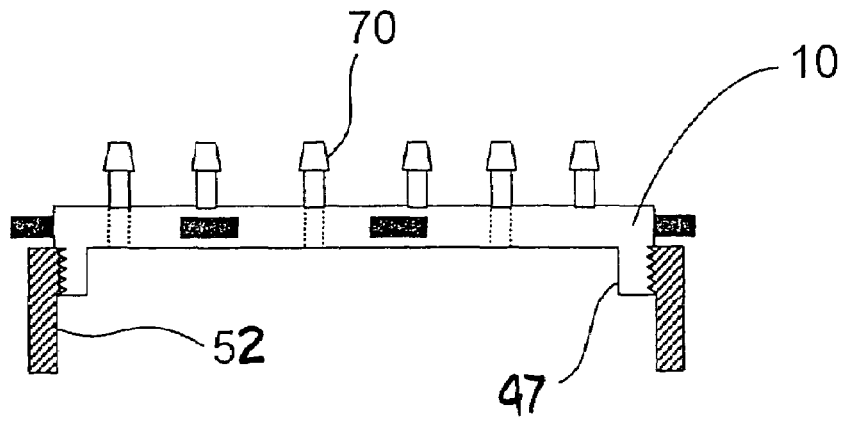

Although the sampling head 10 is structured to fit snugly within a host port 52, to prevent it from being popped into or out of the port during use, additional mechanical restraints are highly desirable. As shown, in FIG. 4, this is accomplished by means of a threaded collar 40 that engages with and holds an annular lip 45 provided on the head 10, when said collar 40 is screwed into the port 52 of the receptacle 50. Other mechanical restraints—such as clamps, screws, bolts, or mated interlocking parts—are known in the art. Alternatively, as shown in FIG. 4A, the head 10 itself may have a skirt 46 depending outwardly from the first face 12 and a series of threads 53 designed to mate with the threads 54 of the port 52. The skirt 46 may use threads on its inner surface so it mates with threads on the outer surface of the port 52 as shown FIG. 4A or the skirt 47 may have outer threads 53 on its outer surface designed to mate with inner threads 54 of the port 52 as shown in FIG. 4B. The mechanical restraints are preferably temporary mechanical devices that allow easy removal and disposal of spent devices.

As mentioned, the sample containers used for the present invention are preferably flexible bags, particularly so when the fluid sampling device is intended for use in biopharmaceutical applications or like applications that have comparatively high sterile or aseptic requirements. Unlike many conventional sampling devices, the fluid sampling device 100 of the present invention does not rely on valves, pumps, and like mechanisms to promote, urge, facilitate, or otherwise affect the flow of sample liquid out of the host fluid receptacle 50 into an available sample container 130. Rather, fluid flows naturally through the sterile flow path of the device 100 by ambient gravitational forces or internal pressure of the fluid receptacle 50. Preferably it is initially provided in a collapsed state; the flexible bag (or functionally-equivalent expansible fluid container) simply expands, decompresses, or otherwise "fills-out" as withdrawn sample fluid flows thereinto. Alternatively, it may be a rigid or flexible but already expanded container and contains a gas or air vent (not shown) such as a hydrophobic membrane-containing filter (an example being a Millex® vent filter available from Millipore Corporation of Billerica, Mass.) that allows the air or other gas to escape as the fluid enters the container. By using the filter, one also renders the vent sterile against bacterial ingress.

Although the use of a flexible, bag-like sample container 130 is preferred, a rigid sample container can also be used without departing from objectives of the present invention. For example, the sample container can be configured as a spacious, rigid box, bulb, vial, syringe or bottle. The vent as described above or as described below can be provided to permit the displacement of contained gas as sample fluid flows thereinto.

Another type of vent (not shown) that can be implemented with little cost, yet still provide good aseptic functionality, is constructed by "patching" and opening the rigid container (i.e., above the expected fluid fill level thereof) with a gas permeable sheet of fluoropolymer membrane (e.g., "Gore-Tex"-brand membrane available from WI. L. Gore and Associates of Wilmington, Del.) or a substantially gas permeable sheet of polyethylene fiber (e.g., "Tyvek"-brand material available from E.I. du Pont de Nemours, Inc. of Wilmington, Del.).

As an alternative to complete rigidity, it is envisioned that a sample container comprise rigid side walls that bend and flex along folds or creases or crumple zones, and the like, such that the sample container is capable of collapsing or otherwise diminishing its volume. Examples of collapsible rigid configurations include accordion-like configurations, bellows-like configurations, and other configurations having pleated side walls.

The mechanisms underlying the operation of the fluid sampling device 100 call for a certain rigidity in the configuration of switches 32 as well as the sampling head 10. Aside from durability, the rigidity allows the switches 32 to be pushed into their open positions with sufficient and appropriate force to overcome the frictional forces that create the liquid tight seal, without the switch 32 flexing, bending, crumpling, or otherwise deforming, such circumstances potentially leading to sampling failures, and/or more catastrophically, breach of extant sterile conditions.

Because several openings 30 are provided through the head 10, physical space immediately outside the head will likely be cramped, and may not accommodate sample containers 130 large enough to collect the volumes of fluid desired. Hence, the sample containers 130 are placed further geographically downstream of the ports 16, with lengths of conduit material 120 provided there between. A flexible conduit such as a plastic, rubber or silicone tube is a preferred embodiment of the conduit although other conduits such as rigid plastic or metal, such as stainless steel can be used.

Although a flexible conduit 120 and the ports 16 can be formed as one component, in all likelihood, the conduits 120 and ports—owing to their differing preferred material composition—are formed separately. For example, in one embodiment, conduits 120 are made of flexible elastomeric material such as silicone, whereas the ports 16 are made of high-impact, rigid polymeric material. In such and like instances, each port 16 can be provided with means for securely attaching the flexible conduit, such as the barbed end 70 shown in FIGS. 3 and 4, 4A and 4B or a Luer fitting (not shown) or any other such connection device know n to one of ordinary skill in the art.

In the preferred configuration, a locking device (not shown) can be provided to prevent the switch 32 from being premature moved into its open position, as well as prevent it from being moved too far past or away from its said position. While such means will vary depending on the ultimate configuration of the fluid sampling device an anchor can be provided to prevent the switch 32 from being pushed into its open position prematurely. When sampling is commenced, the anchor can be moved into a position in which it no longer impedes the transit of the switch 32 through the head 10. When pushed in, switch 32 prevents the switch from being pushed in too far. A bump or raised portion (not shown) can also be provided on the front end of the switch 32 to prevent the switch 32 from being pulled out. Other means can also be used to limit the movement of the switch 32 so as to prevent its being pulled out.

For applications having comparatively strict sterility requirements (e.g., biopharmaceutical applications), the present invention is preferably embodied in kit form, comprising, enclosed within sterile packaging, the following principal kit contents: (a) a pre-sterilized port insert constructed in accordance with any embodiment described and/or otherwise enabled herein; (b) a supply of pre-sterilized flexible tubing, preferably "pre-cut to length", connected or connectable to the elongate members of said port insert; and (c) a supply of pre-sterilized sample containers connected or connectable to said flexible tubing, the pre-sterilized sample containers also constructed in accordance with any embodiment described and/or otherwise enabled herein. It is preferred that the kit be preassembled and then sterilized in its bag or container, using well known means such as gamma radiation, beta radiation, ethylene oxide gas and the like. The provision of the present invention in kit form advances certain objectives either not possible or difficult to accomplish otherwise. Foremost, the kit assures that all its contents are pre-sterilized, and essentially remain so until use. Further, ease of installation, assembly, and operation are improved since all kit contents are pre-selected, pre-sized, and pre-matched to assure proper fit and assembly. And, along similar lines, a kit-based approach promotes standardization of the kit's contents, as well as their manufacture and packaging, leading to reduced product costs, fostering the product's "disposability", and broadening the accessibility of the technology to the public.

Optionally, the kit may also contain, for example, means for locking the port insert within the port provided on a host fluid receptacle; accessories and other means used for assembling the fluid sampling device (e.g., clamps, connectors, junctions, manifolds, and the like); means for mounting, fixing, and/or positioning the assembled fluid sampling device relative to the host receptacle (e.g., adhesive strips, fasteners, brackets, and the like); and a disposal bag for disposing a spent fluid sampling device. These and other optional kit contents, if included, are all sterilized in their packaging. Both the principal and optional kit contents can be provided, if desired, individually or collectively wrapped (i.e., in groups) within said sterile packaging, thus providing additional sterile barriers.

Although certain embodiments of the invention are disclosed, those skilled in the art, having the benefit of the teaching of the present invention set forth herein, can affect numerous modifications thereto. These modifications are to be construed as encompassed within the scope of the present invention as set forth in the appended claims.

The invention claimed is:

1. A fluid sampling device comprising: a sampling head, the head having a first and a second major face on opposite sides from each other, the head having a plurality of openings extending through it from the first major face to the second major face, each of the openings adjacent the second face has an attachment port to which a fluid conduit is attached downstream of the second face and port, each conduit having a collection receptacle in fluid communication with the conduit and being downstream of the conduit, each opening adjacent the first major face having a recess that extends in a plane parallel to the first and second major faces, each recess having a movable switch which selectively covers the opening in a manner allowing movement of said switch between a "closed" and an "open" position in the recess and wherein the device from a side of each switch facing the second major face through the collection receptacle is sterile before each switch is moved from its closed to its open position.

2. The fluid sampling device of claim 1, wherein each recess has a means for providing a water-tight seal with the opening and the recess wherein the means is selected from the group consisting of O-rings and gaskets.

3. The fluid sampling device of claim 1, wherein each recess has a means for providing a water-tight seal with the opening and the recess wherein the means is selected from the group consisting of O-rings and gaskets in each recess.

4. The fluid sampling device of claim 1, wherein each recess has a means for providing a water-tight seal with the opening and the recess wherein the means is selected from the group consisting of O-rings and gaskets on each switch.

5. The fluid sampling device of claim 1 wherein the switch has a hole and a solid portion, the hole having a diameter equal to or less than the diameter of the opening, the hole being in alignment with the opening when the switch is in the open position and the solid portion being in alignment with the opening when the switch, is in the closed position.

6. A fluid sampling kit for retrieving a fluid sample from a fluid receptacle in a sterile manner, the fluid receptacle provided with a port, the fluid sampling kit comprising, enclosed within sterile packaging, a pre-sterilized fluid sampling device comprising a sampling head having a first and a second major face on opposite sides from each other, the head having a plurality of openings extending through it from the first major face to the second major face, each of the openings adjacent the second, face has an attachment port to which a pre-sterilized fluid conduit is attached downstream of the second face and attachment port, each conduit having a pre-sterilized collection receptacle in fluid communication with the conduit and being downstream of the conduit, each opening adjacent the first major face having a recess that extends in a plane parallel to the first and second major faces, each recess having a movable switch which selectively covers the opening in a manner allowing movement of said switch between a "closed" and an "open" position in the recess.

7. The fluid sampling kit of claim 6 wherein the switch has a hole and a solid portion, the hole having a diameter equal to or less than the diameter of the opening, the hole being in alignment with the opening when the switch is in the open position and the solid portion being in alignment with the opening when the switch is in the closed position.

8. The fluid sampling kit of claim 6 further comprising each recess has a water-tight seal with the opening and recess and the water-tight seal is selected from the group consisting of O-rings and gaskets.

9. The fluid sampling kit of claim 6 wherein the switch is moved in a direction selected from the group consisting linear and rotationally in the plane parallel to the first and second major surfaces.

10. A fluid sampling device comprising: a sampling head, the head having a first and a second major face on opposite sides from each other, the body having a plurality of openings extending through it from the first major face to the second major face, each of the openings adjacent the second face has an attachment port to which a fluid conduit is attached downstream of the second face and port, each conduit having a collection receptacle in fluid communication with the conduit and being downstream of the conduit, each opening adjacent the first major face having a recess that extends in a plane parallel to the first and second major faces, each recess having a movable switch which selectively covers the opening in a manner allowing movement of said switch between a "closed" and an "open" position in the recess and wherein the device from a side of each switch facing the second major face through the collection receptacle is sterile before each switch is moved from its closed to its open position and each recess has a water-tight seal with the opening and recess.

11. The fluid sampling device of claim 10 wherein the water-tight seal is selected from the group consisting of O-rings and gaskets.

12. The fluid sampling device of claim 10 wherein the switch is moved in a direction selected from the group consisting linear and rotationally in the plane parallel to the first and second major surfaces.

13. The fluid sampling device of claim 10 wherein the switch has a hole and a solid portion, the hole having a diameter equal to or less than the diameter of the opening, the hole being in alignment with the opening when the switch is in the open position and the solid portion being in alignment with the opening when the switch is in the closed position.

\* \* \* \* \*

UNITED STATES PATENT AND TRADEMARK OFFICE
CERTIFICATE OF CORRECTION

| | | |
|---|---|---|
| PATENT NO. | : 7,578,205 B2 | Page 1 of 1 |
| APPLICATION NO. | : 11/441910 | |
| DATED | : August 25, 2009 | |
| INVENTOR(S) | : Brett M. Belongia | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 572 days.

Signed and Sealed this

Seventh Day of September, 2010

David J. Kappos
*Director of the United States Patent and Trademark Office*